Figure 1:
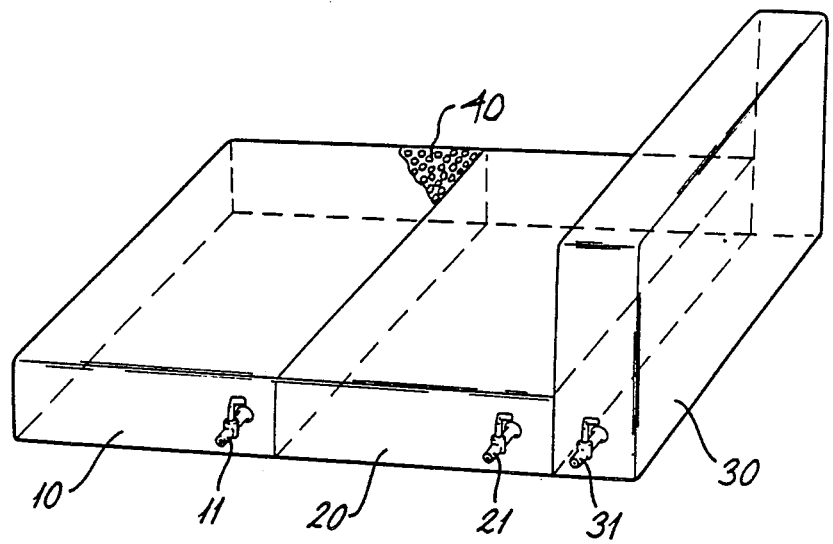
Figure 2A:
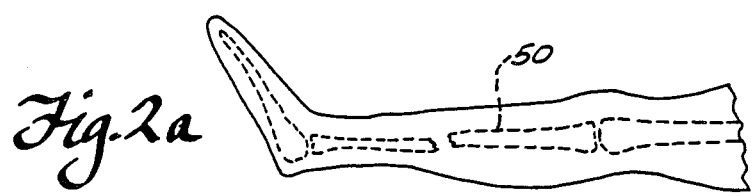
Figure 2B:
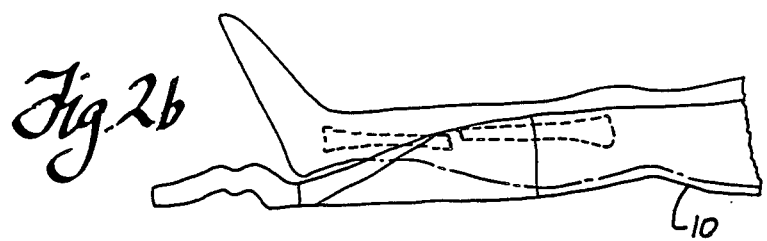
Figure 2C:
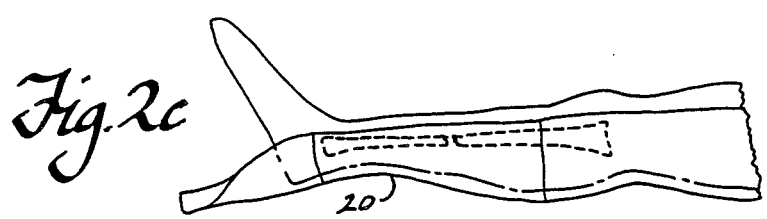
Figure 2D:
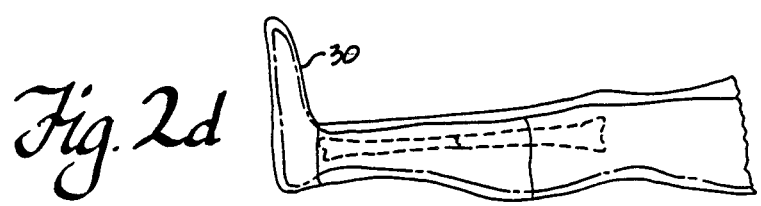
Figure 2E:
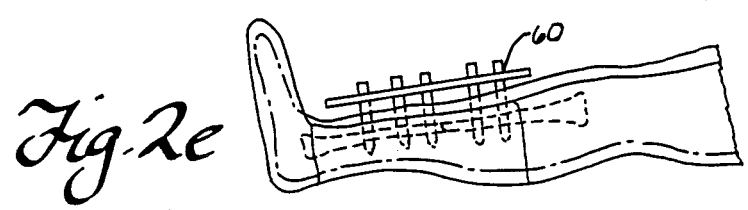

United States Patent [19]

Coombs

[11] Patent Number: 4,862,879
[45] Date of Patent: Sep. 5, 1989

[54] ORTHOPAEDIC SPLINTS

[75] Inventor: Richard R. H. Coombs, Kingston, England

[73] Assignee: National Research Development Corporation, London, England

[21] Appl. No.: 217,123

[22] Filed: Jul. 7, 1988

Related U.S. Application Data

[62] Division of Ser. No. 821,335, Jan. 22, 1986, abandoned.

[30] Foreign Application Priority Data

Jan. 24, 1985 [GB] United Kingdom ............... 8501838

[51] Int. Cl.⁴ ............................................. A61F 5/04
[52] U.S. Cl. ........................... 128/87 R; 128/92 Z; 128/DIG. 20
[58] Field of Search .................... 128/78, 83, 90, 119, 128/92 R, 92 Z, 92 VD, DIG. 20

[56] References Cited

U.S. PATENT DOCUMENTS

| | | | |
|---|---|---|---|
| 2,531,074 | 11/1950 | Miller | 128/DIG. 20 X |
| 3,631,854 | 1/1972 | Fryer | 128/90 |
| 3,643,656 | 2/1972 | Young et al. | 128/90 |
| 3,745,998 | 7/1973 | Rose | 128/89 |
| 3,762,404 | 10/1973 | Sakita | 128/DIG. 20 X |
| 3,905,376 | 9/1975 | Johnson et al. | 128/90 X |
| 4,120,297 | 10/1978 | Rabischong et al. | 128/78 |
| 4,192,502 | 3/1980 | Owen | 272/119 |
| 4,320,749 | 3/1982 | Highley | 128/83 |
| 4,393,867 | 7/1983 | Baron | 128/87 R |
| 4,442,834 | 4/1984 | Tucker | 128/90 |
| 4,498,467 | 2/1985 | Kirkpatrick | 128/90 |

FOREIGN PATENT DOCUMENTS

| | | |
|---|---|---|
| 926722 | of 0000 | United Kingdom . |
| 1095311 | of 0000 | United Kingdom . |
| 1101076 | of 0000 | United Kingdom . |
| 1422966 | of 0000 | United Kingdom . |
| 2108849 | of 0000 | United Kingdom . |

OTHER PUBLICATIONS

European Search Report.
British Search Report.

*Primary Examiner*—Robert A. Hafer
*Assistant Examiner*—Charles H. Sam
*Attorney, Agent, or Firm*—Cushman, Darby & Cushman

[57] ABSTRACT

An orthopeadic splint comprises a plurality of self-contained compartments (10, 20, 30) having flexible impermeable walls, each compartment containing fluent granular material and being provided with a valve (11, 21, 31) allowing evacuation and inflation respectively to solid and deformable conditions, the compartments being connected serially with a common wall portion between each successive pair of compartments.

1 Claim, 2 Drawing Sheets

ORTHOPAEDIC SPLINTS

This is a division of application Ser. No. 821,335, filed Jan. 22, 1986, which was abandoned upon the filing hereof.

This invention concerns orthopaedic splints for use in association with external fixation devices for bone fractures.

These last devices are of a kind involving a set of components variably connectable with each other and the fragments of a fractured bone by way of bone pins to form a support holding the fragments in a desired positional relationship for the purposes of reunion.

Some of these devices are designed to cater for a considerable variety of fracture and related situations. Such devices are relatively complex in form and usage, and commonly comprise an extensive range of components including universal couplings and other adjustment mechanisms whereby the device can adopt a great many geometrical configurations. A particular feature of these devices is a mode of use whereby the device is applied to the bone fragments and thereafer adjusted to align and reduce the fracture, whereat the device is clamped. This mode of use can be very difficult in the absence of appropriate experience and expertise on the part of the operating personnel and, even then, can be very time consuming.

Other external fixation devices of the kind in question are designed for use in a lesser variety of, but nevertheless more commonly occurring situations, typically those involving fractures in the long bones of the limbs and especially in the leg. These devices are relatively simple in form, and so significantly less costly, but they are still not satisfactory in all respects for their intended purposes. More particuarly, there is a much reduced adjustability and it is therefore normally appropriate to align and reduce the fracture manually as best possible before application of the device. This procedure can be problematical insofar as the position to which the fracture is manipulated must be held during device application and this requires close co-operation between suitably skilled multiple personnel.

An object of the invention is to facilitate the device application procedures above, particularly for those devices of relatively simple form, and to this end there is provided an orthopaedic splint comprising a plurality of self-contained compartments having walls which are flexible and impermeable, each said compartment containing fluent granular material and each having closable port means allowing evacuation and return of air from and to the associated compartment respectively to render the same solid and deformable, said compartments being connected serially with a common wall portion between each successive pair of compartments.

In an initially developed form of the invention there are three compartments arranged, when unfolded, with the two compartments at one end and middle of the serial connection in general alignment, and the remaining compartment at the other end of such connection extending transversely thereto to form an L-shaped overall assembly.

This form of the invention is intended for use in fixing a long bone fracture in the lower leg, particularly in the tibia, in association with a device of the above simple form.

In such use the splint is located in its deformable condition with the one end, middle and remaining end compartments respectively extending behind the knee, behind the lower leg long bones and under the foot. The one end compartment is wrapped around the knee and evacuated to immobilise the same, and more particularly to immobilise the upper fragment of the fractured long bone relative to the knee and upper leg. The lower leg is them manipulated to align the fracture and the middle compartment thereafter wrapped round the lower leg and evacuated to immobilise the same and more particularly to immobilise the lower fragment of the fractured bone relative to the upper fragment in a rotational sense. Lastly, the foot is raised to reduce the fracture and the remaining compartment wrapped around the foot and evacuated to immobilise the same. The associated device can thereafter be applied and clamped, and the splint removed following release by admission of air to its compartments.

The wrapping of the compartment in this use must, of course, be such as to allow appropriate access of the bone pins of the device to the limb without puncturing the compartments but this is not incompatible with the desired immobilisation, the latter being possible without complete envelopment of the lower limb. Thus at least some of the wrapping can be such as to provide a trough-like configuration.

The accompanying drawings diagrammatically illustrates a presently preferred embodiment of the form of splint just described and serve to clarify the invention and its use by way of example.

FIG. 1 diagrammatically illustrates, with a part broken away, a presently preferred embodiment of the invention, and FIGS. 2a–2e similarly illustrate use of such an embodiment.

The illustrated splint has three compartments 10, 20 and 30 having walls which are flexible and impermeable. Each compartment contains fluent granular material shown at 40 in FIG. 1, and has a like respective port means 11, 21 and 31 including a manually-operable valve to open and close the void space of the compartment interior to atmosphere. These port means allow evacuation of each compartment on an individual basis by connection, when the associated valve is opened, with a vacuum pump effectively to solidify the compartment by consequent compaction of the contained granular material to a friction-locked non-fluent mass and compaction of the surrounding walls on to such mass. Clearly, this solidification can be sustained by closing the port valve before disconnecting the vacuum pump and this state can be released to return the compartment to deformability by opening the port valve to readmit air.

The three compartments 10, 20 and 30 are serially connected with a common wall portion between each pair of successive compartments. More particularly the compartments are each of slab form, with compartments 10 and 20 being of like dimensions and connected in end-to-end manner, and with compartment 30 being shorter and connected across the end of the compartment 20 which is otherwise free to project transversely therefrom in an overall L-shape for the splint.

The intended use of this embodiment has already been described above, but this use is clarified by FIGS. 2a–2e which show a leg with a fractured tibia 50, in FIG. 2b application of the splint and evacuation of compartment 10 to immobilise the knee and the upper tibial fragment, in FIG. 2c evacuation of compartment 20 to immobilise the lower tibial fragment following manipulation of this fragment into alignment, in FIG. 2d evacuation of compartment 30 to immobilise the foot following elevation of the latter to reduce the tibial fracture, and in FIG. 2e application of an external fixation device 60, whereafter the splint can be removed it is appropriate to note additional details pertinent to this use.

The dimensions of the compartments clearly should suit the use and, as a guide, it is proposed that the length, width and depth be about 40, 40 and 10 cms for compartments 10 and 20, and about 10, 40 and 30 cms for compartment 30, to suit an adult patient.

The compartment walls should be made of a material which is compatible with appropriate medical cleansing, and should also be X-ray transmissive to allow visualisation of the fracture under manipulation. These requirements are readily met by plastics materials already in medical usage, such as polyolefins.

The granular material should also meet similar requirements and, again, existing materials, such as polysytrene beads, are suitable.

While the invention has been described with particular reference to the illustrated embodiments and a specific usage, this is not intended to be limiting. Clearly, other forms and applications for the splint are possible within the introductory discussion thereof above.

Also, while the invention has been conceived initially to facilitate application of a simple form of external fixation device, application of a complex form of device can also be facilitated by allowing immobilisation of a fracture in a disposition effected by preliminary manual manipulation, with the device being applied thereafter to require only fine adjustent following splint removal.

I claim:

1. A process for using an orthopaedic splint in association with an external fixation device to set a fracture in a long bone of a limb:

said splint including a plurality of self-contained compartments having walls which are flexible and impermeable, each said compartment containing fluent granular material and each having respective closable port means allowing evacuation and return of air from and to the associated compartment respectively to render the same solid and deformable, said compartments being connected serially with a common wall portion between each successive pair of compartments:

said device including an elongate structure and a plurality of bone pins, said pins being connectable between respective locations successively extending along said structure and corresponding locations along said bone; and said process comprising:

locating said splint, with said port means open, adjacent said limb with one said compartment alongside one end portion of said bone on one side of said fracture and the next succeeding said compartment alongside the other end portion of said bone on the other side of said fracture;

wrapping said one compartment about said limb, evacuating the same and closing the respective port means to immobilize said bone one end portion;

manipulating said bone other end portion to align the same with said bone one end portion;

wrapping said next compartment about said limb, evacuating the same and closing the respective port means to immobilize said bone other end portion in its aligned state;

connecting said device with said bone with some of said pins connected to locations in said bone one end portion and others of said pins connected to locations in said bone other end portions; and thereafter opening said port means and removing said splint to leave said bone retained with its end portions aligned by said device.

* * * * *